(12) United States Patent
Harrison

(10) Patent No.: US 6,832,636 B2
(45) Date of Patent: Dec. 21, 2004

(54) FUEL NOZZLE LEVER, A FUEL NOZZLE AND A METHOD OF OPERATING A FUEL NOZZLE

(76) Inventor: Graeme Harrison, 313 Seven Hills Road, Seven Hills, NSW 2147 (AU)

( * ) Notice: Subject to any disclaimer, the term of this patent is extended or adjusted under 35 U.S.C. 154(b) by 212 days.

(21) Appl. No.: 10/256,487

(22) Filed: Sep. 26, 2002

(65) Prior Publication Data

US 2003/0056617 A1 Mar. 27, 2003

Related U.S. Application Data

(60) Provisional application No. 60/325,506, filed on Sep. 27, 2001.

(51) Int. Cl.$^7$ .............................. B65B 1/04; B65B 3/00; B67C 3/00
(52) U.S. Cl. .............................. 141/392; 141/98; 141/1; 251/90; 251/234
(58) Field of Search ................................ 141/1, 97, 98, 141/392; 251/90–92, 231, 232, 234, 293

(56) References Cited

U.S. PATENT DOCUMENTS

| | | |
|---|---|---|
| 2,396,459 A | 3/1946 | Dana |
| 2,707,377 A | 5/1955 | Morrison |
| 2,834,187 A | 5/1958 | Loveday |
| 2,900,800 A | 8/1959 | Loveday |
| 2,967,152 A | 1/1961 | Matsch et al. |
| 3,030,780 A | 4/1962 | Loveday |
| 3,114,469 A | 12/1963 | Francis et al. |
| 3,147,877 A | 9/1964 | Beckman |
| 3,166,511 A | 1/1965 | Matsch et al. |
| 3,298,185 A | 1/1967 | Loudon |
| 3,481,504 A | 12/1969 | Nelson |
| 3,583,592 A | 6/1971 | Kerfman |
| 3,698,589 A | 10/1972 | Perry |
| 3,948,409 A | 4/1976 | Ovchinnikov et al. |
| 4,176,695 A | 12/1979 | Raske |
| 4,201,253 A | 5/1980 | Maloney |
| 4,216,807 A | 8/1980 | Diamond |
| 4,275,776 A | 6/1981 | Rehkopf |
| 4,718,239 A | 1/1988 | Nowobilski et al. |
| 4,802,516 A | 2/1989 | Dahlem |
| 4,846,447 A | 7/1989 | Hanna |
| 5,040,769 A * | 8/1991 | Wilber et al. .................. 251/90 |
| 5,217,054 A | 6/1993 | Mollica |
| 5,386,706 A | 2/1995 | Bergsten et al. |
| 5,613,366 A | 3/1997 | Schoenman |
| 6,122,920 A | 9/2000 | Hill et al. |
| 6,273,157 B1 | 8/2001 | Molnar |
| 6,279,621 B1 | 8/2001 | Gelsomino |

FOREIGN PATENT DOCUMENTS

| | | |
|---|---|---|
| AU | 200061328 A1 | 3/2001 |
| GB | 2319514 A | 11/1996 |

\* cited by examiner

Primary Examiner—Timothy L. Maust
(74) Attorney, Agent, or Firm—Clayton, Howarth & Cannon, P.C.

(57) ABSTRACT

A lever for use with a fuel nozzle having a trigger disposed intermediate a hand piece and a hand guard, the trigger being laterally displaceable toward the hand piece so as to actuate a fuel flow. The lever includes an elongate member having a handle on one end and a fulcrum located adjacent an opposite end. The fulcrum is adapted to engage the hand guard. The lever also includes a bearing configured to engage the trigger such that, in use, the handle is rotatable about the fulcrum so as to displace the trigger toward the hand piece.

44 Claims, 11 Drawing Sheets

FUEL NOZZLE LEVER, A FUEL NOZZLE AND A METHOD OF OPERATING A FUEL NOZZLE

CROSS-REFERENCE TO RELATED APPLICATIONS

This application claims the benefit of U.S. Provisional Application No. 60/325,506, filed Sep. 27, 2001, which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates to the dispensing of fuel and in particular to a fuel nozzle lever, a fuel nozzle and a method of operating a fuel nozzle.

2. Description of Related Art

The present invention has been developed primarily for use when dispensing fuel from a self-serve fuel station and will be described with reference to this application. However, it will be appreciated that the invention is not limited to this particular field of use.

The vast majority of prior art fuel nozzles share some basic design features. They generally have a hand piece which is gripped by the user's palm, allowing the user's fingers to squeeze a trigger toward the hand piece to actuate a fuel flow. Typically the trigger is biased toward the closed position. Hence, if a user wishes to maintain fuel flow for an extended period, for example to fill up the tank of a car, it is necessary to maintain the squeezing pressure on the trigger for an extended period.

It has been appreciated by the inventor that the prior art nozzles and the above described method of operation can present significant difficulties for those with reduced hand strength, for example the elderly and people with hand related disabilities such as rheumatoid or osteoarthritis or broken bones. Indeed, even people with merely a smaller than average hand span can experience difficulties. Such people can experience problems such as cramping, discomfort and pain when continuously squeezing a fuel nozzle trigger for an extended time. Further, people who are particularly susceptible to these type of problems may be unable to effectively operate fuel nozzles at all.

A partial solution to this problem is provided by some prior art nozzles which include a latch which can be used to maintain the trigger in the open position without the necessity of exerting any force. The latch can subsequently be disengaged once the required amount of fuel has been dispensed. However many jurisdictions have passed laws banning the used of latches, especially in self serve fuel stations where the customer is entrusted with the operation of the fuel nozzle. An example, of such a restriction is provided by Australian Standard AS1940-1993 6.4.2. This provision effectively restricts the use of latches, including objects such as fuel caps or keys, which keep the nozzle in an open state to fuel stations which are not of the "self serve" variety.

It has been further appreciated by the inventor that the prior art design of fuel nozzles encourages the user to grip and actuate the nozzle using a power grip. This is the type of grip which involves holding an object between the flexed fingers and the palm. Such a grip is not well suited to those suffering from a lack of hand strength or a hand related disability.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY OF THE INVENTION

It is an advantage of the present invention to overcome or ameliorate at least one of the drawbacks of the prior art, or to provide a useful alternative.

Accordingly, in a first aspect, the invention provides a lever for use with a fuel nozzle having a trigger disposed intermediate a hand piece and a hand guard, said trigger being laterally displaceable toward said hand piece so as to actuate a fuel flow, said lever including:

an elongate member having a handle disposed adjacent a distal end and a fulcrum disposed adjacent a proximate end, said fulcrum being adapted to engage said hand guard; and nozzle engagement means connected to said elongate member, said nozzle engagement means including a bearing disposed for engagement with said trigger such that, in use, the handle is rotatable with respect to said fulcrum so as to displace said trigger toward said hand piece.

According to a second aspect of the invention there is provided a lever for use with a fuel nozzle having a trigger disposed intermediate a hand piece and a hand guard, said trigger being laterally displaceable toward said hand piece so as to actuate a fuel flow, said lever including:

an elongate member having a handle disposed adjacent a distal end and nozzle engagement means disposed adjacent a proximate end, said nozzle engagement means including a bearing disposed for engagement with said hand guard; and a fulcrum connected to said elongate member intermediate said distal and proximate ends, said fulcrum being engagable with said trigger such that, in use, the handle is rotatable about said fulcrum so as to displace said trigger toward said band piece.

Both of the above arrangements advantageously reduce the stresses associated with continuously maintaining a nozzle trigger in an open position. Desirably, the lever allows a user to operate the nozzle using a precision grip rather than a power grip. A precision grip involves pinching an object between the flexor aspect of the fingers and that of the opposing thumb and is a type of grip which is far more suited to people suffering hand impairment and lack of strength.

The preferred embodiment is designed to ensure that the biasing of the trigger pushes the lever to a retracted position if continuous pressure is not applied to the handle whilst in operation, thereby stopping fuel flow. This is aided by the use of a bearing on the nozzle engagement means by minimizing the friction associated with rotating the lever between the extended and retracted positions. Hence, the invention is more likely to meet the requirements of Australian Standard AS1940-1993 6.4.2., as mentioned above. The minimisation of friction provided by the bearing also assists in the use of the lever by those with lesser hand strength.

According to a third aspect of the invention there is provided a fuel nozzle adapted to selectively control a flow of fuel from a reservoir and out of an aperture provided in the nozzle, said flow being regulated by a valve which is, in turn, regulated by the position of an elongate member rotatably mounted to said nozzle, and wherein said elongate member may have a length of greater than about 12 cm.

The length of the elongate member assists in operation of the fuel nozzle by those with lesser hand strength by increasing the mechanical advantage. In one preferred embodiment, the length of the elongate member may exceed 15 cm.

According to another aspect of the invention there is provided a method of operating a fuel nozzle having a trigger disposed intermediate a hand piece and a hand guard, said trigger being laterally displaceable toward said hand piece so as to actuate a fuel flow, said method including the steps of:

providing a lever in accordance with either the first or second aspects of the invention;

ensuring that the nozzle engagement means is in a retracted position;

engaging the fulcrum with the nozzle;

rotating the handle such that the nozzle engagement means engages the nozzle;

rotating the handle such that the nozzle engagement means is in an extended position, thereby causing fuel to flow through said nozzle; and rotating the handle such that the nozzle engagement means returns to the retracted position, thereby stopping the fuel flow.

Additional advantages of the invention will be set forth in the description which follows, and in part will be apparent from the description, or may be learned by the practice of the invention without undue experimentation. The advantages of the invention may be realized and obtained by means of the instruments and combinations particularly pointed out in the appended claims.

BRIEF DESCRIPTION OF THE DRAWINGS

The above and other features and advantages of the invention will become apparent from a consideration of the subsequent detailed description presented in connection with the accompanying drawings in which.

DETAILED DESCRIPTION OF THE INVENTION

Figure 1:
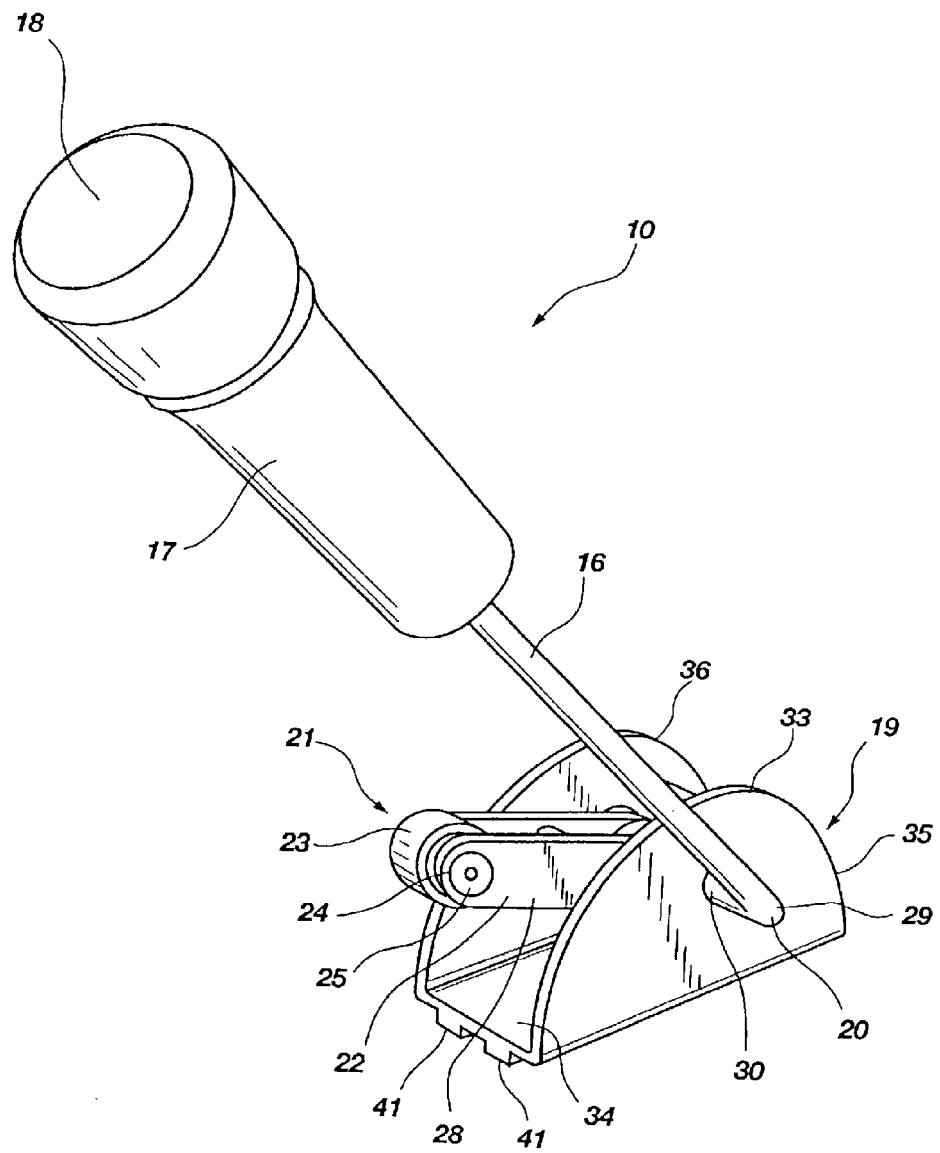
FIG. 1 is a perspective view of one embodiment of the invention.
Figure 2:
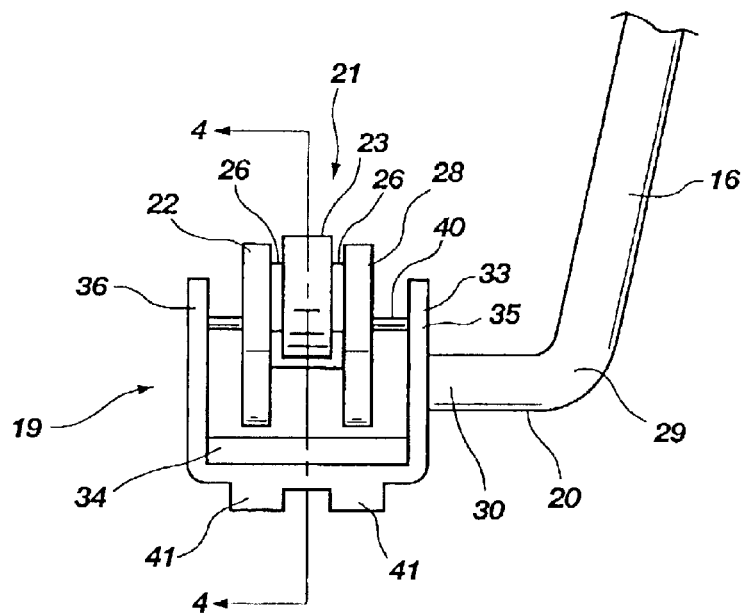
FIG. 2 is a partial front view of the embodiment shown in FIG. 1.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

It is to be understood that embodiments of the invention having dimensions differing from those shown in all of the figures, may nevertheless still fall within the scope of the invention.

Figure 7:
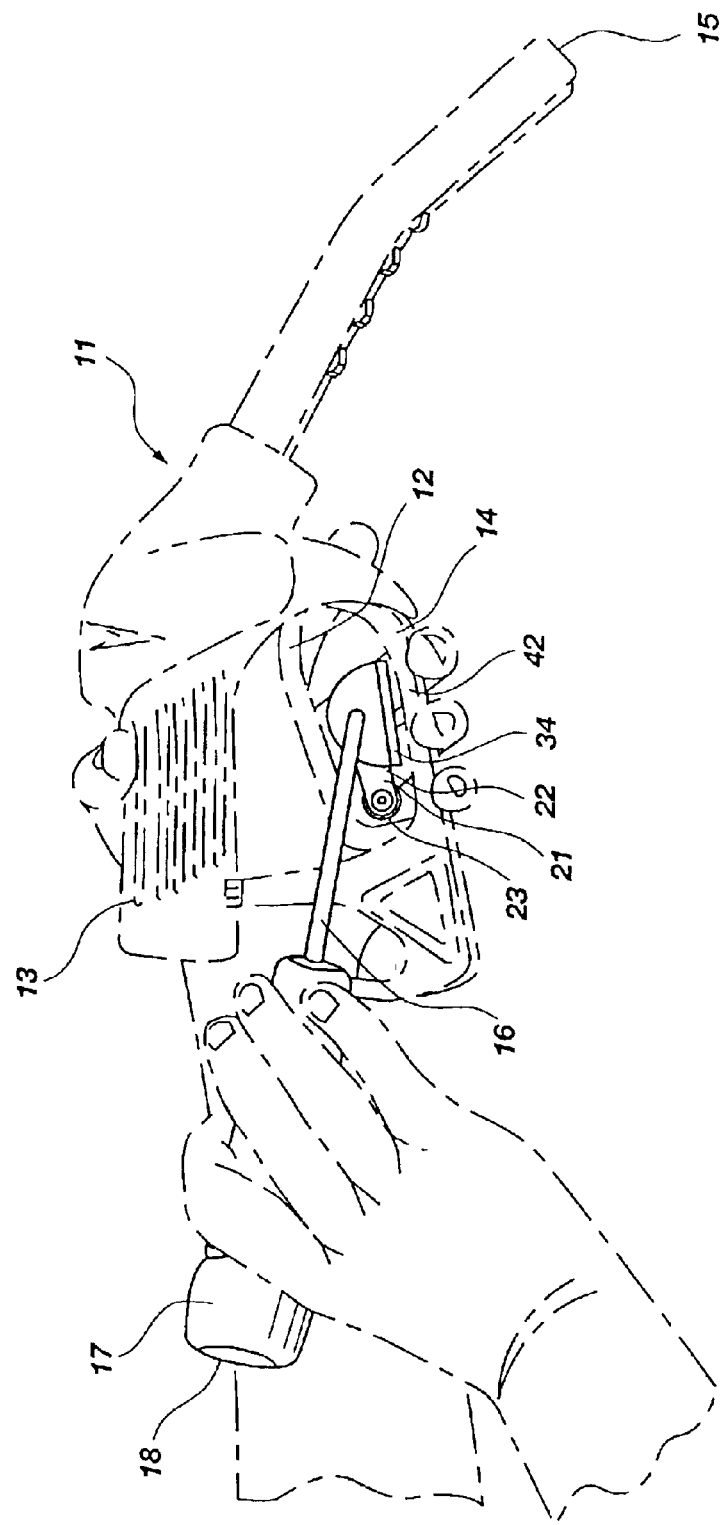
FIG. 7 is a side view of the embodiment prior to actuation of a trigger.
Figure 8:
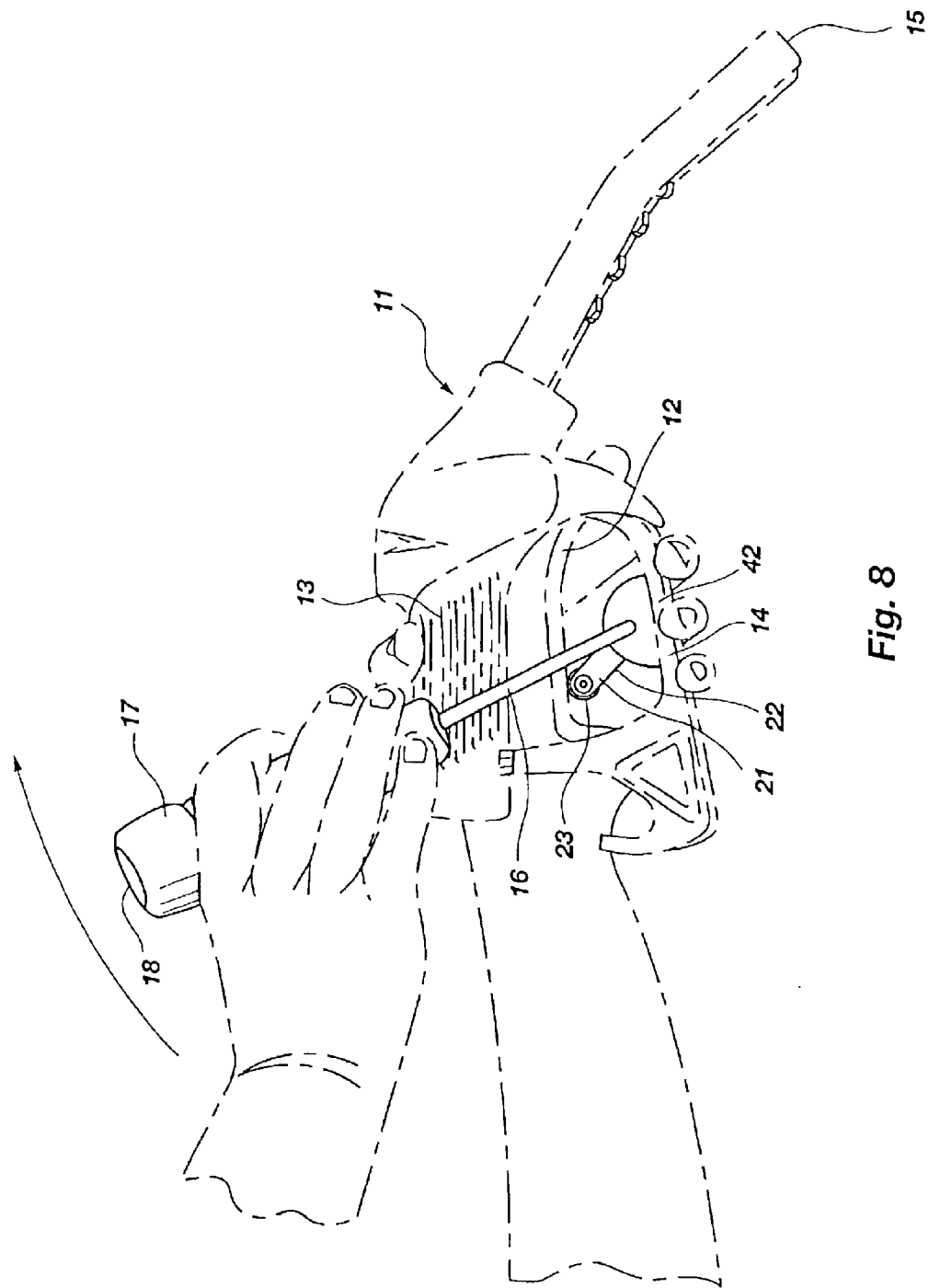
FIG. 8 is a side view of the embodiment during actuation of a trigger.
Figure 9:
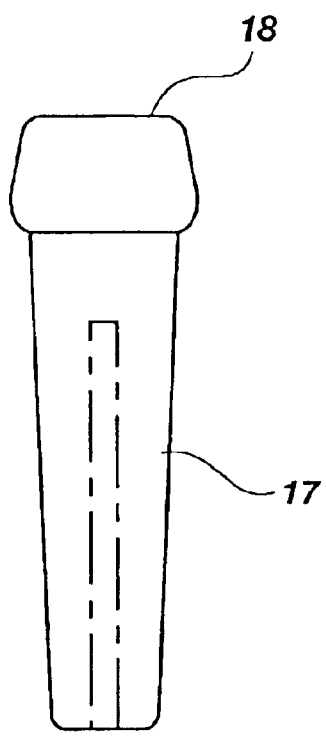
FIG. 9 is a plan view of a handle in accordance with the invention.
Figure 10:
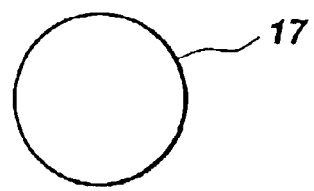
FIG. 10 is a plan view of the handle shown in FIG. 9.
Figure 11:
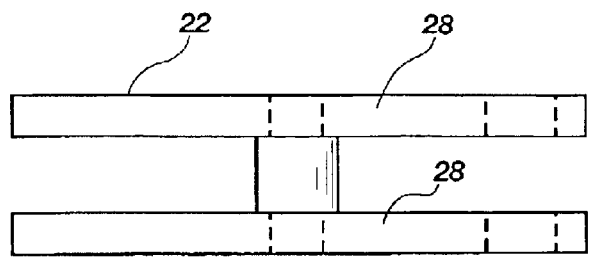
FIG. 11 is a plan view of a swing arm for use in the embodiment of the present invention.
Figure 12:
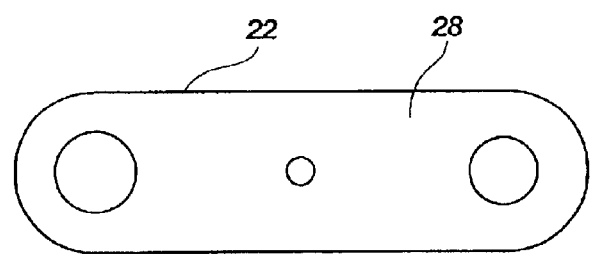
FIG. 12 is a side view of the swing arm shown in FIG. 11.
Figure 13:
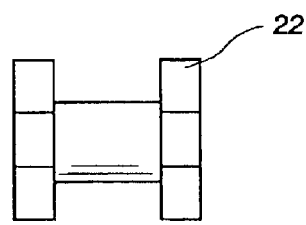
FIG. 13 is an end view of the swing arm shown in FIG. 11.
Figure 14:
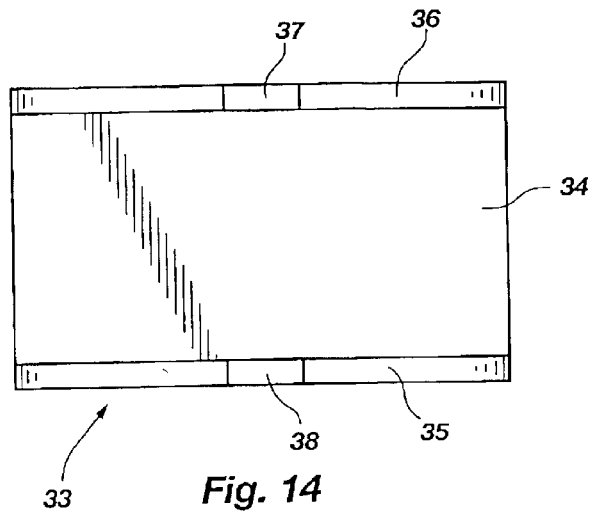
FIG. 14 is a plan view of a frame for use in one embodiment of the present invention.
Figure 15:
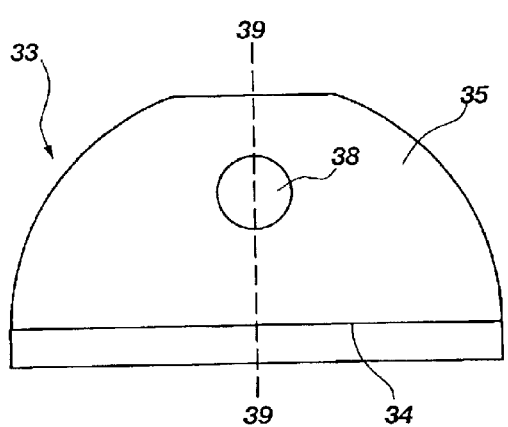
FIG. 15 is a side view of the frame shown in FIG. 14.
Figure 16:
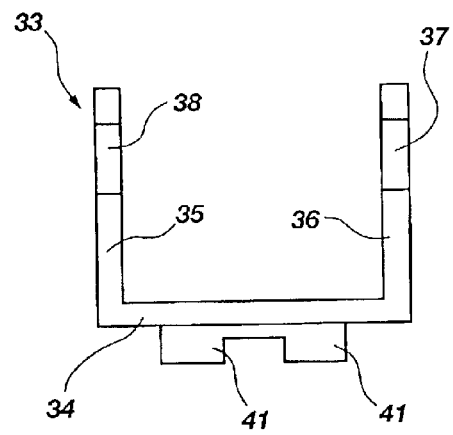
FIG. 16 is an end view of the frame shown in FIG. 14.

The lever, indicated generally at 10, is for use with a fuel nozzle 11 shown in phantom in FIGS. 7 and 8. The fuel nozzle 11 has a trigger 12 disposed intermediate a hand piece 13 and a hand guard 14. The trigger 12 is laterally displaceable toward the hand piece 13 so as to actuate a fuel flow out of nozzle aperture 15.

The lever 10 has an elongate member 16 which includes a handle 17 disposed adjacent a distal end 18 and a fulcrum, indicated generally at 19, disposed at a proximal end 20 of the elongate member 16. As such, the elongate member 16 is adapted to engage the hand guard 14 as shown in FIGS. 7–8. The engagement of the fulcrum 19 with the hand guard 14 may be either a removable engagement or a fixed engagement, as desired. It will be appreciated that the term "elongate member" as referred to herein is not restricted to linear members, but may also include members having bend portions within the scope of the present invention.

The lever 10 also includes nozzle engagement means, indicated generally at 21, connected to the elongate member 16 and adapted to engage the trigger 12 such that, in use, the handle 17 is rotatable about the fulcrum 19 so as to displace the trigger 12 towards the hand piece 13. This arrangement advantageously provides a user with alternative means to actuate the trigger of pre-existing fuel nozzles.

In an alternative embodiment (not illustrated and hereinafter referred to as "the reversed embodiment") the fulcrum 19 is disposed intermediate the distal 18 and proximate 20 ends and is adapted to engage the trigger. In such an embodiment the nozzle engagement means 21 is adapted to engage the hand guard 14. The reversed embodiment provides for a different lever type to that utilized by the illustrated embodiment.

In some embodiments the handle 17 is not a separate part of the elongate member 16, but rather the handle 17 is formed by, or is an integral part of, the elongate member 16.

In the illustrated embodiment the nozzle engagement means 21 includes a swing arm 22 which, in use, extends from the fulcrum 19 to the trigger 12, as shown in FIG. 8.

Figure 18:
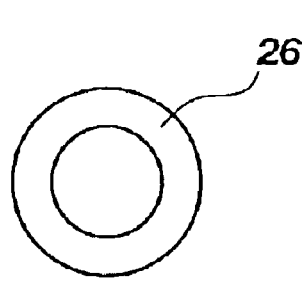
FIG. 18 is a side view of a spacer used in one embodiment of the present invention.
Figure 17:
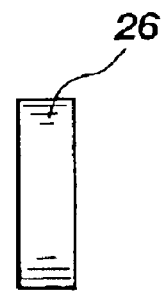
FIG. 17 is a plan view of a spacer used in one embodiment of the present invention.
Figure 19:
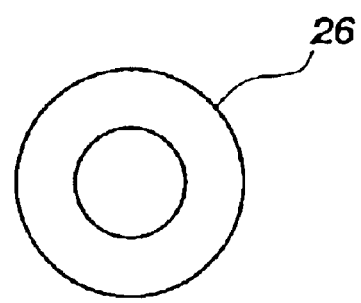
FIGS. 19 is a side view of a spacer used in one embodiment of the present invention.
Figure 20:
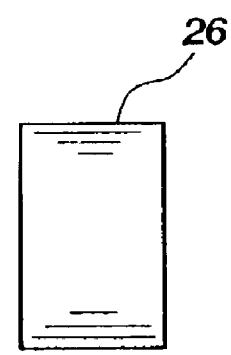
FIG. 20 is a plan view of a spacer used in one embodiment of the present invention.

As shown in FIG. 1, a bearing 23 is disposed adjacent an end 24 of the swing arm 22. The bearing 23 is engagable with the trigger 12 and may help to reduce friction as the bearing 23 rolls along the trigger 12 as the handle is rotated. The bearing 23 may be rotatably disposed upon the end 24 of the swing arm 22 by means of a bolt 25 and a pair of spacers 26. The spacers 26 are best shown in FIGS. 17 and 18 and may be disposed upon a shaft 27 which extends between the two opposing side walls 28 of the swing arm 22 so as to maintain the bearing 23 generally central of the swing arm side walls 28. To further minimize friction the spacers 26 may be fabricated from brass or other materials having low friction properties. In the reversed embodiment the bearing 23 may be engagable with the hand guard 14. It will be appreciated by those skilled in the art that the bearing 23 may include a stationary surface that is not rotatable, in addition to a rotatable bearing within the scope of the present invention.

Figure 5:
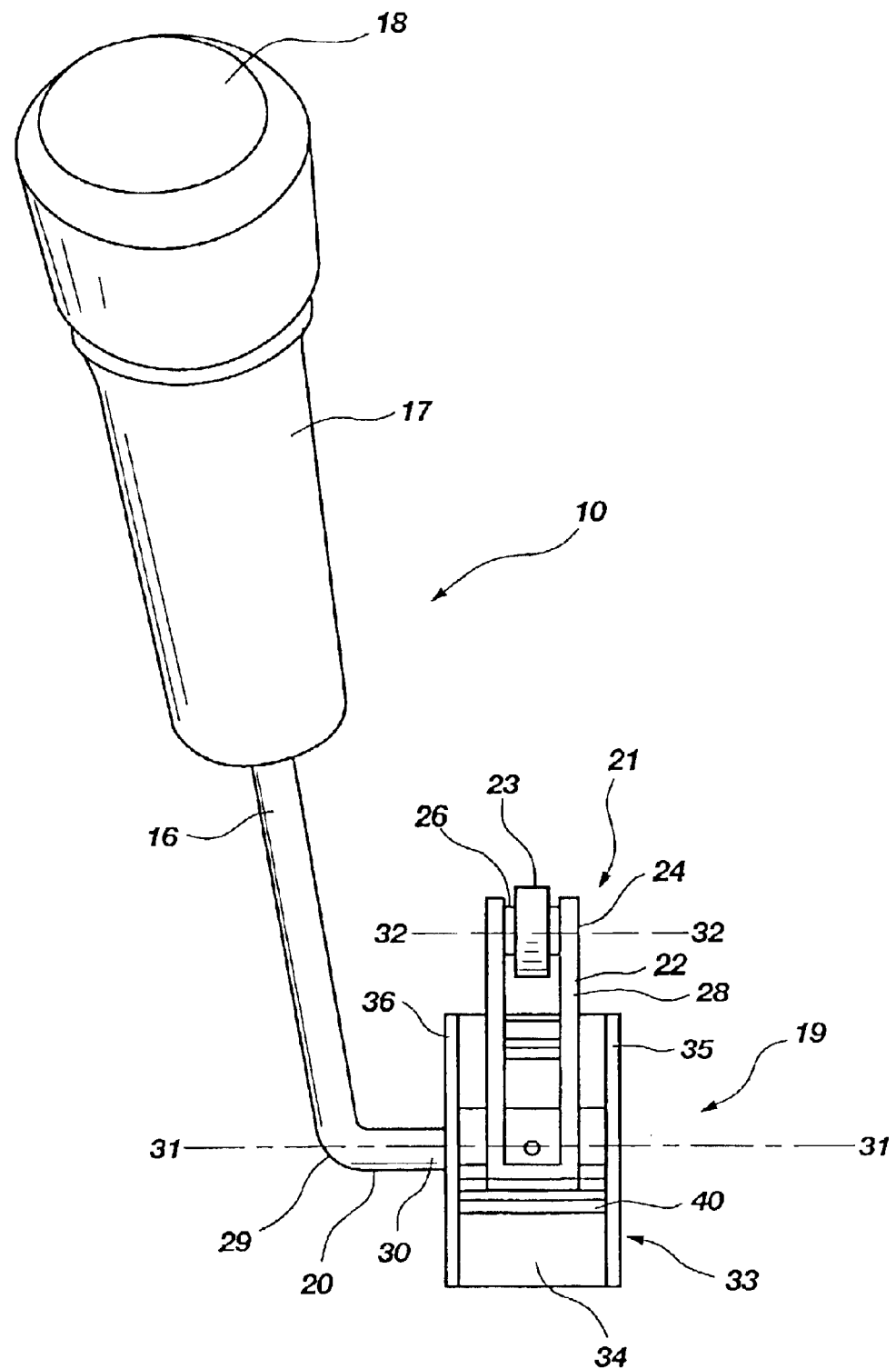
FIG. 5 is a plan view of the embodiment shown in FIG. 1.
Figure 6:
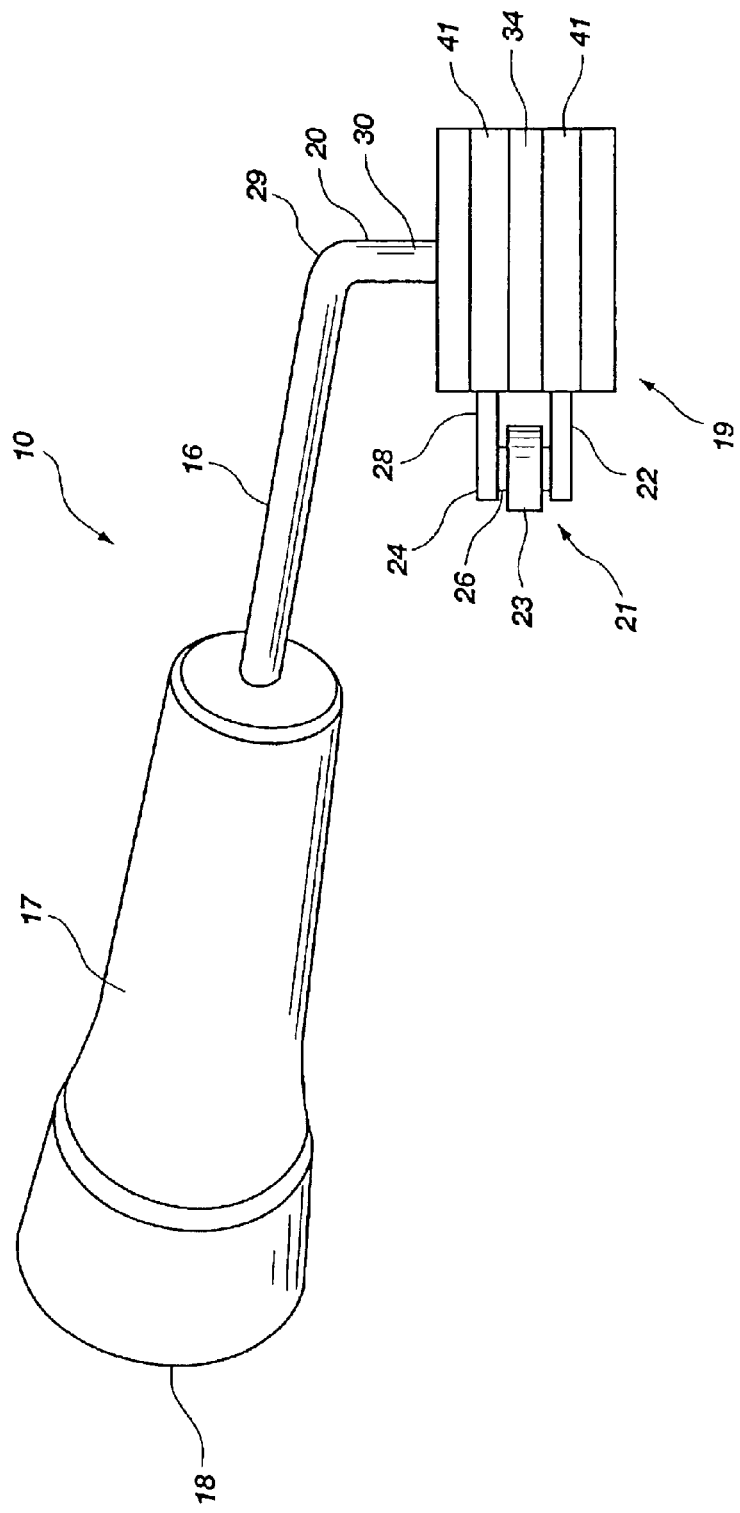
FIG. 6 is an underside view of the embodiment shown in FIG. 1.

The elongate member 16 may be a substantially cylindrical rod having a bend 29 adjacent the proximal end 20 to define an axle 30 at the proximate end. The axle 30 forms an axis of rotation of the fulcrum 19. In other words, both the elongate member 16 and the nozzle engagement means 21 rotate as one about the axis of rotation given by axle 30. This axis of rotation is shown diagrammatically on FIG. 5 by line 31—31. The bearing 23 may be mounted for rotation about an axis which is substantially parallel to axle 30. The axis of rotation of the bearing 23 is shown diagrammatically on FIG. 5 as line 32—32.

The axle 30 may be rotatably mounted to a frame 33 which includes a base 34 which is adapted to engage the hand guard 14. The base 34 connects two spaced apart opposing side walls 35 and 36. The side walls respectively define apertures 37 and 38 adapted to rotatably mount the axle 30 to the frame 33. The handle 17 is rotatable with respect to the frame 33 so as to rotate the nozzle engagement means 21 between a retracted position (as shown in FIG. 7) in which the nozzle engagement means 21 is substantially parallel with the base 34 and an extended position (illustrated in FIG. 8) in which the nozzle engagement means 21 is rotated towards a normal of the base 34. This normal is shown diagrammatically by line 39—39. As illustrated in FIG. 7, the retracted position provides sufficient clearance for the fulcrum 19 and associated frame 33 to be inserted between the trigger 12 and the hand guard 14. During rotation of the nozzle engagement means 21 into the extended position shown in FIG. 8, the end of the nozzle engagement means 21 travels through an arc which causes bearing 23 to roll along the trigger 12. This also has the affect of laterally displacing the trigger 12 so as to actuate a fuel flow from aperture 15 of the fuel nozzle 11. It will be appreciated that in the reversed embodiment the bearing 23 rolls along the hand guard 14.

When in the extended position, the nozzle engagement means 21 may make an angle of between 30 degrees and 80 degrees with the base 34. More preferably the angle is the range of 60 degrees to 70 degrees and, in the preferred embodiment, this angle is approximately 65 degrees. The frame 33 may include a stop 40 adapted to restrain the nozzle engagement means 21 from rotating beyond the extended position. In the illustrated embodiment the stop 40 is in the form of a formation extending between the frame side walls 35 and 36. In other embodiments the stop 40 is a formation extending from one or other of the frame side walls 35 or 36. In the illustrated embodiment the formation takes the form of a cylindrical rod. The stop 40 ensures that the nozzle engagement means 21 does not go "over center". This ensures that the trigger 12 cannot be inadvertently locked in the open position which would effectively cause the lever 10 to function as a latch. Rather, the biasing of the trigger 12 toward the closed position transfers a force to the nozzle engagement means 21 tending to push it towards the retracted position. In other words, the lever 10 only functions to maintain the trigger 12 in the open position whilst a force is being exerted upon the handle by a user. Once such a force is removed, the biasing of the trigger 12 is sufficient to rotate the nozzle engagement means 21 out of the way to enable the trigger 12 to automatically close, thereby halting the fuel flow.

The base 34 may include one or more formations 41 adapted to promote secure engagement between the base 34 and the hand guide 14. In the illustrated embodiment the formations 41 take the form of one or more longitudinally extending ribs spaced so as to releasably mate with a channel 42 defined by the hand guard 14. In the reversed embodiment the base 34 is adapted to securely engage the trigger 12.

The relative lengths of the elongate member 16 (inclusive of the handle 17) and the nozzle engagement means 21 (inclusive of the bearing 23) are preferably selected to confer a mechanical advantage to the user when using the lever 10 to actuate the trigger 12. In particular, the ratio of the length of the elongate member (inclusive of the handle) to the length of the nozzle engagement means 21 (inclusive of the bearing) preferably exceeds 2:1. More preferably, said ratio exceeds 4:1 and in the embodiment illustrated the ratio is approximately 6:1. In the illustrated embodiment the elongate member 16 has an effective length of approximately 24 centimeters and the nozzle engagement means 21 has an effective length of approximately 4 centimeters.

Figure 3:
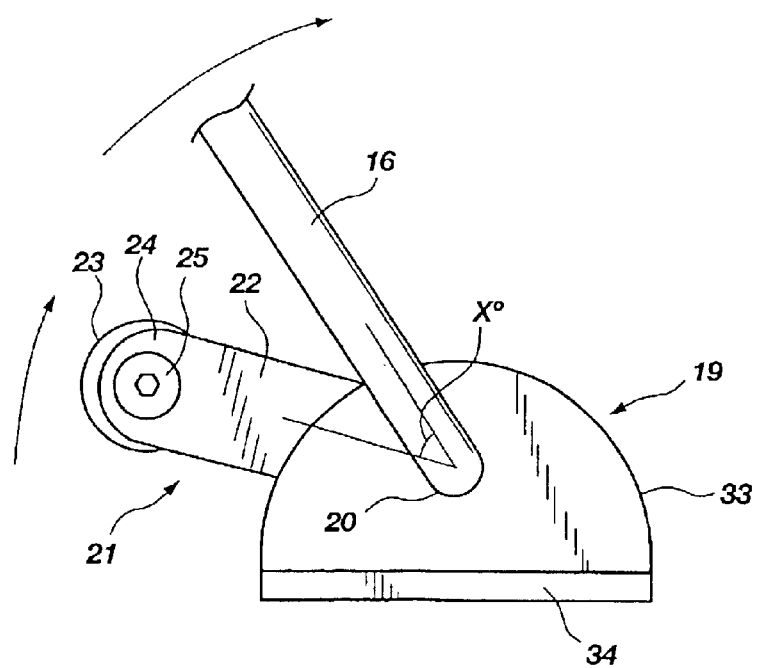
FIG. 3 is a partial side view of the embodiment shown in FIG. 1.
Figure 4:
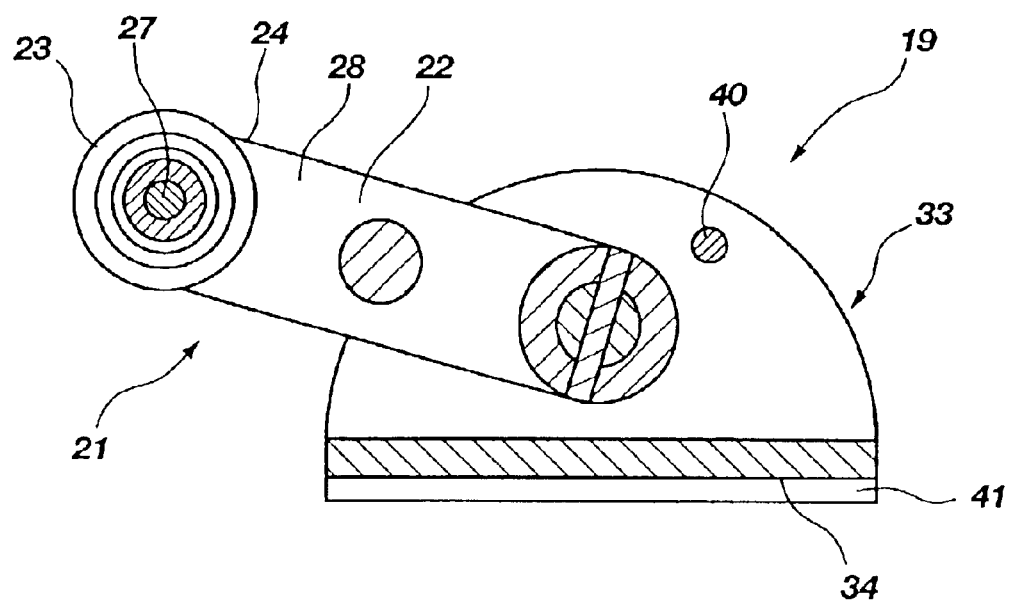
FIG. 4 is a sectioned view of the embodiment taken through line 4—4 of FIG. 2.

The nozzle engagement means 21 is preferably off-set from the elongate member 16 by between 1 degree and 60 degrees. This angle is marked in FIG. 3 as x° and, in the illustrated embodiment, is approximately 40 degrees. In an alternative embodiment (not illustrated) said angle is approximately 10 degrees. This off-set angle can be adjusted as necessary to ensure that the handle 17 does not foul against a vehicle receiving petrol as the nozzle engagement means 21 is rotated between the retracted and extended positions. Additionally, the side of the frame from which the elongate member 16 extends can be swapped either to ensure that there is sufficient clearance from the vehicle or to adapt the lever 10 for use by left or right handed users.

The lever 10, as shown in the figures, may be portable and adapted for use with any one of a plurality of fuel nozzles. Hence, a motorist can store the lever 10 in their car, and then when the time comes to fill the tank of their vehicle with fuel they can use the lever 10 in conjunction with one of the nozzles at whatever service station they happen to visit. Alternatively, self service fuel stations can make levers 10 available for any members of the public who may find them to be of assistance, or may fix the levers 10 to the nozzles.

The handle 17 may be shaped to encourage a user to adopt a precision grip when gripping the handle. More particularly, it can be seen in FIGS. 7 and 8 that the natural grip that would be assumed by a user when rotating the handle 17 into the extended position is to clasp the handle between the tips of the fingers and the thumb. As discussed above, this type of grip is more appropriate for people suffering from hand disabilities. Another embodiment (not illustrated) of the invention is a fuel nozzle adapted to selectively control a flow of fuel from a reservoir and out of an aperture provided in the nozzle, the flow being regulated by a valve which is, in turn, regulated by the position of an elongate member rotatably mounted to the nozzle. Thus, this arrangement provides an easily actuated lever which forms an integral part of the mechanisms controlling the flow of the nozzle. In such a fuel nozzle, the length of the elongate member is greater than 12 centimeters and preferably greater than 15 centimeters. The elongate member may include a handle disposed on a distal end. Alternatively, the elongate member can itself function as a handle. The handle may be shaped to encourage a user to adopt a precision grip when gripping the handle. With reference to the illustrated embodiment, one method of operating a fuel nozzle includes the following steps: providing a lever 10 in accordance with either of the embodiments; ensuring that the nozzle engagement means 21 is in the retracted position; engaging the fulcrum 19 with the nozzle; rotating the handle 17 such that the nozzle engagement means 21 engages the nozzle; rotating the handle 17 such that the nozzle engagement means 21 is in the extended position, thereby causing fuel to flow through the nozzle; and, once sufficient fuel has been obtained, rotating the handle such that the nozzle engagement means 21 returns to the 9 retracted position thereby stopping the fuel flow. If using a portable lever 10, the method may include the further step of detaching the lever from the nozzle 11. In another aspect of the method the user assumes a precision grip when operating the handle 17.

Although the invention has been described with reference to specific examples, it will be appreciated by those skilled in the art that the invention may be embodied in many other forms.

It will be appreciated that the structure and apparatus disclosed herein is merely one example of a nozzle engagement means, and it should be appreciated that any structure, apparatus or system for engaging a nozzle which performs functions the same as, or equivalent to, those disclosed herein are intended to fall within the scope of a nozzle engagement means, including those structures, apparatus or systems for engaging a nozzle which are presently known, or which may become available in the future. Anything which functions the same as, or equivalently to, a nozzle engagement means falls within the scope of this element.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A lever for use with a fuel nozzle having a trigger disposed intermediate a hand piece and a hand guard, said trigger being laterally displaceable toward said hand piece so as to actuate a fuel flow, said lever including:

an elongate member having a handle disposed adjacent a distal end of said elongate member and a fulcrum disposed adjacent a proximate end of said elongate member, said fulcrum being adapted to engage said hand guard; and nozzle engagement means connected to said elongate member, said nozzle engagement means including a bearing disposed for engagement with said trigger such that, in use, the handle is rotatable with respect to said fulcrum so as to displace said trigger toward said hand piece.

2. The lever according to claim 1 wherein said nozzle engagement means includes a swing arm which, in use, extends from said fulcrum to said trigger.

3. The lever according to claim 2 wherein said bearing is disposed adjacent an end of the swing arm.

4. The lever according to claim 1 wherein said elongate member is a substantially cylindrical rod having a bend adjacent the proximate end to define an axle at said proximate end, said axle forming an axis of rotation of said fulcrum.

5. The lever according to claim 4 wherein said bearing is mounted for rotation about an axis substantially parallel to said axle.

6. The lever according to claim 4 wherein said axle is rotatably mounted to a frame.

7. The lever according to claim 6 wherein said frame includes a base adapted to engage said hand guard, the base connecting two spaced apart opposing sidewalls.

8. The lever according to claim 7 wherein said side walls respectively define apertures adapted to rotatably mount said axle to said frame.

9. The lever according to claim 7 wherein said handle is rotatable with respect to said frame so as to rotate said nozzle engagement means between a retracted position in which said nozzle engagement means is substantially parallel with said base and an extended position in which said nozzle engagement means is rotated towards a normal of said base.

10. The lever according to claim 9 wherein the nozzle engagement means makes an angle of between 30 degrees and 80 degrees with the base when in said extended position.

11. The lever according to claim 7 wherein said base includes one or more formations adapted to promote secure engagement between said base and said hand guard.

12. The lever according to claim 11 wherein said formations include one or more longitudinally extending ribs spaced so as to releasably mate with a channel defined by the hand guard.

13. The lever according to claim 9 wherein said frame includes a stop adapted to restrain said nozzle engagement means from rotating beyond said extended position.

14. The lever according to claim 12 wherein said stop is a formation extending from either or both of said side walls.

15. The lever according to claim 1 wherein the ratio of the length of the elongate member inclusive of the handle to the length of the nozzle engagement means inclusive of the bearing exceeds 2:1.

16. The lever according to claim 1 wherein the nozzle engagement means is offset by between 1 degree and 60 degrees from the elongate member.

17. The lever according to claim 1 wherein said bearing is configured to roll upon contact with said trigger.

18. The lever according to claim 1 wherein said lever is portable and is adapted for use with any one of a plurality of said fuel nozzles.

19. The lever according to claim 1 wherein said lever is adapted to be formed integrally with said nozzle.

20. The lever according to claim 1 wherein the handle is shaped to encourage a user to adopt a precision grip when gripping the handle.

21. A fuel nozzle adapted to selectively control a flow of fuel from a reservoir and out of an aperture provided in the nozzle, said flow being regulated by a valve, said fuel nozzle comprising:
- a lever rotatably mounted to the nozzle for regulating the valve;
- a hand piece;
- a hand guard;
- a trigger disposed intermediate the hand piece and the hand guard; and
- a fulcrum disposed on said lever between said trigger and said hand guard, said fulcrum defining an axis of rotation of said lever, said axis of rotation being spaced apart from said hand guard;
- wherein rotation of said lever about said fulcrum causes said lever to engage said trigger to displace said trigger toward said hand piece.

22. The fuel nozzle according to claim 21 wherein said lever comprises an elongate member having a length greater than 12 cm.

23. The fuel nozzle according to claim 21 wherein said lever includes a handle disposed on a distal end.

24. A nozzle according to claim 23 wherein the handle is shaped to encourage a user to adopt a precision grip when gripping the handle.

25. A method of operating a fuel nozzle having a trigger disposed intermediate a hand piece and a hand guard, said trigger being laterally displaceable toward said hand piece so as to actuate a fuel flow, said method including the steps of:
- providing a lever having an elongate member, a fulcrum and nozzle engagement means;
- engaging the lever with the hand guard;
- engaging the lever with the trigger;
- rotating the elongate member with respect to said fulcrum such that the trigger is displaced toward the hand piece, thereby causing fuel to flow through said nozzle; and
- rotating the elongate member such that the trigger is displaced away from the hand piece, thereby stopping the fuel flow.

26. The method of operating a fuel nozzle according to claim 25 including the further step of detaching the lever from the nozzle.

27. The method of operating a fuel nozzle according to claim 25 wherein the user assumes a precision grip when operating said elongate member.

28. The method of operating a fuel nozzle according to claim 25 wherein engaging the lever with the hand guard further comprises engaging the fulcrum with the hand guard.

29. The method of operating a fuel nozzle according to claim 25 wherein engaging the lever with the trigger further comprises engaging the nozzle engagement means with the trigger.

30. The method of operating a fuel nozzle according to claim 25 further comprising placing the nozzle engagement means in a retracted position prior to engaging the lever with the hand guard.

31. The method of operating a fuel nozzle according to claim 30 wherein rotating the elongate member such that the trigger is displaced toward the hand piece places the nozzle engagement means in an extended position.

32. A lever for use with a fuel nozzle having a trigger disposed intermediate a hand piece and a hand guard, said trigger being laterally displaceable toward said hand piece so as to actuate a fuel flow, said lever comprising:
- an elongate member having a proximate end and a distal end, and nozzle engagement means disposed adjacent said proximate end, said nozzle engagement means including a rotatable bearing for rolling contact with said fuel nozzle so as to displace said trigger toward said hand piece upon rotation of said elongate member.

33. The lever according to claim 32 further comprising a handle disposed adjacent said distal end of said elongate member.

34. The lever according to claim 32 further comprising a fulcrum connected to said elongate member, wherein said elongate member rotates about said fulcrum.

35. The lever according to claim 34 wherein said fulcrum comprises a base and two opposing side walls.

36. The lever according to claim 35 wherein said elongate member forms an axle which extends between said opposing sidewalls.

37. The lever according to claim 36 wherein nozzle engagement means further comprises a swing arm disposed on said axle between said opposing side walls.

38. The lever according to claim 37 wherein said bearing is disposed on an end of said swing arm.

39. The lever according to claim 35 wherein said base comprises at least one formation for securing the base to the hand guard.

40. The lever according to claim 34 wherein said fulcrum comprises a stop to limit movement of the elongate member.

41. The lever according to claim 32 wherein said elongate member has a bend adjacent the proximal end to define an axle at the proximate end.

42. A lever for use with a fuel nozzle having a trigger disposed intermediate a hand piece and a hand guard, said trigger being laterally displaceable toward said hand piece so as to actuate a fuel flow, said lever comprising:
- an elongate member having a proximate end and a distal end, said elongate member forming an axle at said proximate end;
- nozzle engagement means disposed adjacent said proximate end of said elongate member; and
- a fulcrum disposed on said elongate member and configured to be positioned between said hand guard and said trigger, said fulcrum comprising a support for said axle;
- wherein said lever is configured to contact said hand guard and said trigger so as to displace said trigger toward said hand piece upon rotation of said elongate member about said fulcrum.

43. A lever for use with a fuel nozzle having a trigger disposed intermediate a hand piece and a hand guard, said trigger being laterally displaceable toward said hand piece so as to actuate a fuel flow, said lever comprising:
- an elongate member having a proximate end and a distal end;
- nozzle engagement means disposed adjacent said proximate end of said elongate member; and
- a fulcrum disposed on said elongate member and configured to be positioned between said hand guard and said trigger, said fulcrum being rotatable with respect to said elongate member;

wherein at least a portion of said lever is configured to reside between said hand guard and said trigger such that said trigger is disposed within reach of said nozzle engagement means such that movement of said elongate member causes said nozzle engagement means to engage said trigger so as to displace said trigger toward said hand piece.

44. A lever for use with a fuel nozzle having a trigger disposed intermediate a hand piece and a hand guard, said trigger being laterally displaceable toward said hand piece so as to actuate a fuel flow, said lever including:

an elongate member having a handle disposed adjacent a distal end of said elongate member and a fulcrum disposed adjacent a proximate end of said elongate member, said fulcrum being adapted to engage said hand guard;

nozzle engagement means connected to said elongate member, said nozzle engagement means including a bearing disposed for engagement with said trigger;

wherein said nozzle engagement means includes a swing arm which, in use, extends from said fulcrum to said trigger;

wherein said bearing is disposed adjacent an end of the swing arm;

wherein said elongate member is a substantially cylindrical rod having a bend adjacent the proximate end to define an axle at said proximate end, said axle forming an axis of rotation of said elongate member;

wherein said bearing is mounted for rotation about an axis substantially parallel to said axle;

wherein said fulcrum comprises a frame and wherein said axle is rotatably mounted to said frame;

wherein said frame includes a base connecting two spaced apart opposing side walls, said base adapted to engage said hand guard;

wherein said side walls respectively define apertures adapted to rotatably mount said axle to said frame;

wherein said handle is rotatable with respect to said frame so as to rotate said nozzle engagement means between a retracted position in which said nozzle engagement means is substantially parallel with said base and an extended position in which said nozzle engagement means is rotated towards an angle perpendicular to said base;

wherein the nozzle engagement means makes an angle of between 30 degrees and 80 degrees with the base when in said extended position;

wherein said base includes one or more formations adapted to promote secure engagement between said base and said hand guard;

wherein said formations include one or more longitudinally extending ribs spaced so as to releasably mate with a channel defined by the hand guard;

wherein said frame includes a stop adapted to restrain said nozzle engagement means from rotating beyond said extended position;

wherein said stop is a formation extending from at least one of said side walls;

wherein the ratio of the length of the elongate member inclusive of the handle to the length of the nozzle engagement means inclusive of the bearing exceeds 2:1;

wherein the nozzle engagement means is offset by between 1 degree and 60 degrees from the elongate member;

wherein said lever is portable and is adapted for use with any one of a plurality of said fuel nozzles;

wherein the handle is shaped to encourage a user to adopt a precision grip when gripping the handle;

wherein the handle is rotatable with respect to said fulcrum so as to displace said trigger toward said hand piece.

* * * * *